United States Patent
Fujita

(10) Patent No.: US 7,194,061 B2
(45) Date of Patent: Mar. 20, 2007

(54) X-RAY COMPUTER TOMOGRAPHY APPARATUS

(75) Inventor: Hidehiro Fujita, Otawara (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 0 days.

(21) Appl. No.: 11/222,942

(22) Filed: Sep. 12, 2005

(65) Prior Publication Data

US 2007/0025497 A1    Feb. 1, 2007

(30) Foreign Application Priority Data

Sep. 14, 2004   (JP) ............................ 2004-267217

(51) Int. Cl.
*G21K 1/04* (2006.01)
*G21K 1/12* (2006.01)

(52) U.S. Cl. .................... 378/9; 378/150; 378/151

(58) Field of Classification Search .................... 378/4, 378/9, 14–16, 19, 197, 145, 147–153
See application file for complete search history.

(56) References Cited

U.S. PATENT DOCUMENTS

| | | | | |
|---|---|---|---|---|
| 5,966,422 A | * | 10/1999 | Dafni et al. ................ | 378/9 |
| 6,018,562 A | * | 1/2000 | Willson ........................ | 378/9 |
| 6,421,412 B1 | * | 7/2002 | Hsieh et al. .................. | 378/9 |
| 6,980,623 B2 | * | 12/2005 | Dunham et al. ............. | 378/19 |
| 2003/0076920 A1 | * | 4/2003 | Shinno et al. ................ | 378/4 |

FOREIGN PATENT DOCUMENTS

| | | |
|---|---|---|
| JP | 5-168616 | 7/1993 |
| JP | 6-38957 | 2/1994 |

* cited by examiner

*Primary Examiner*—Edward J. Glick
*Assistant Examiner*—Irakli Kiknadze
(74) *Attorney, Agent, or Firm*—Oblon, Spivak, McClelland, Maier & Neustadt, P.C.

(57) ABSTRACT

An X-ray computer tomography apparatus includes a substantially annular rotating frame supported to be rotatable around a rotation axis, a plurality of X-ray tubes discretely provided along the circumference of the rotating frame, a plurality of X-ray detectors discretely provided along the circumference of the rotating frame, a plurality of variable-opening slits which are made to respectively correspond to the plurality of X-ray tubes, and a slit control unit which individually controls the widths and central positions of openings of the plurality of slits.

19 Claims, 7 Drawing Sheets

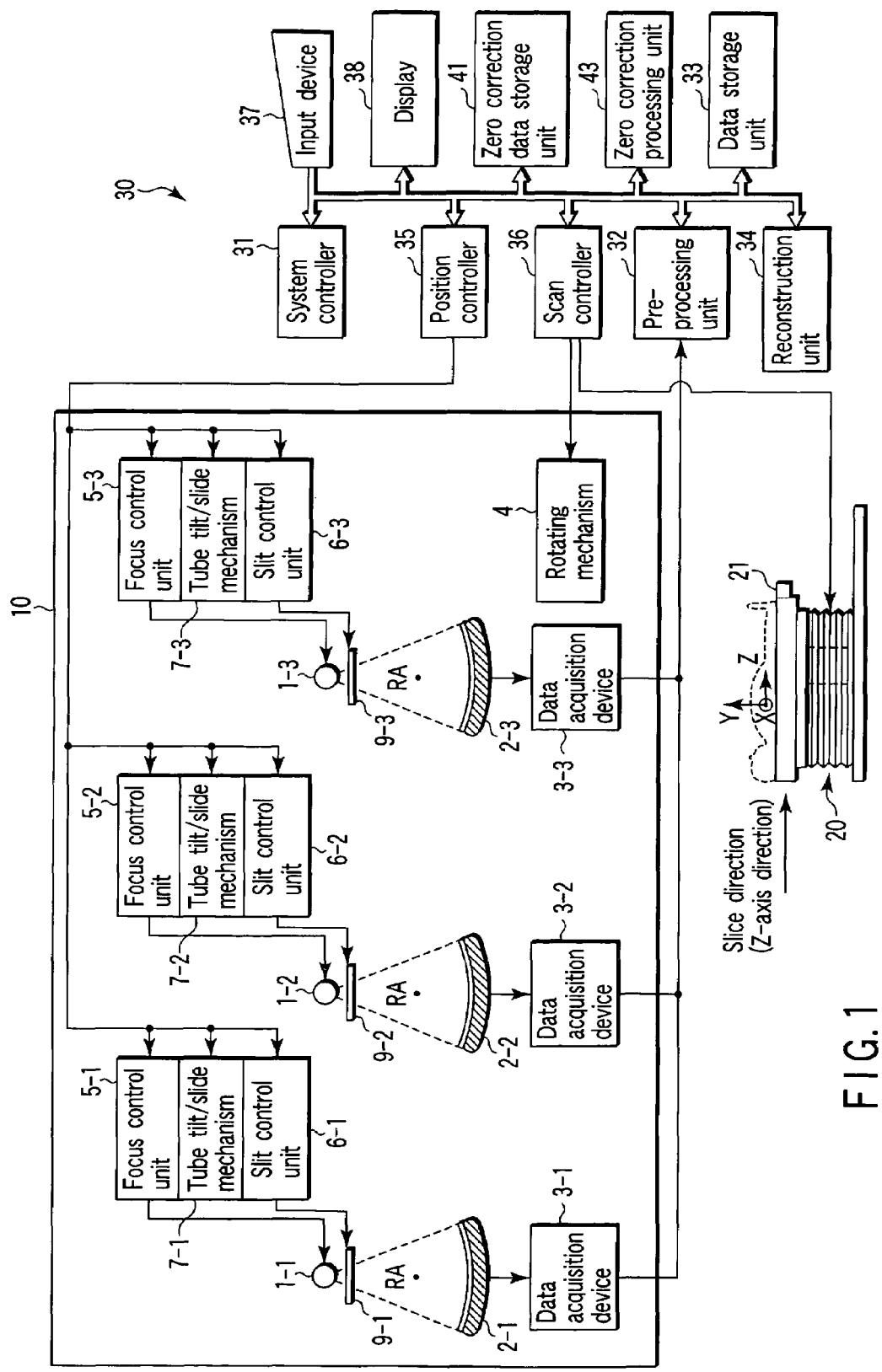
F I G. 1

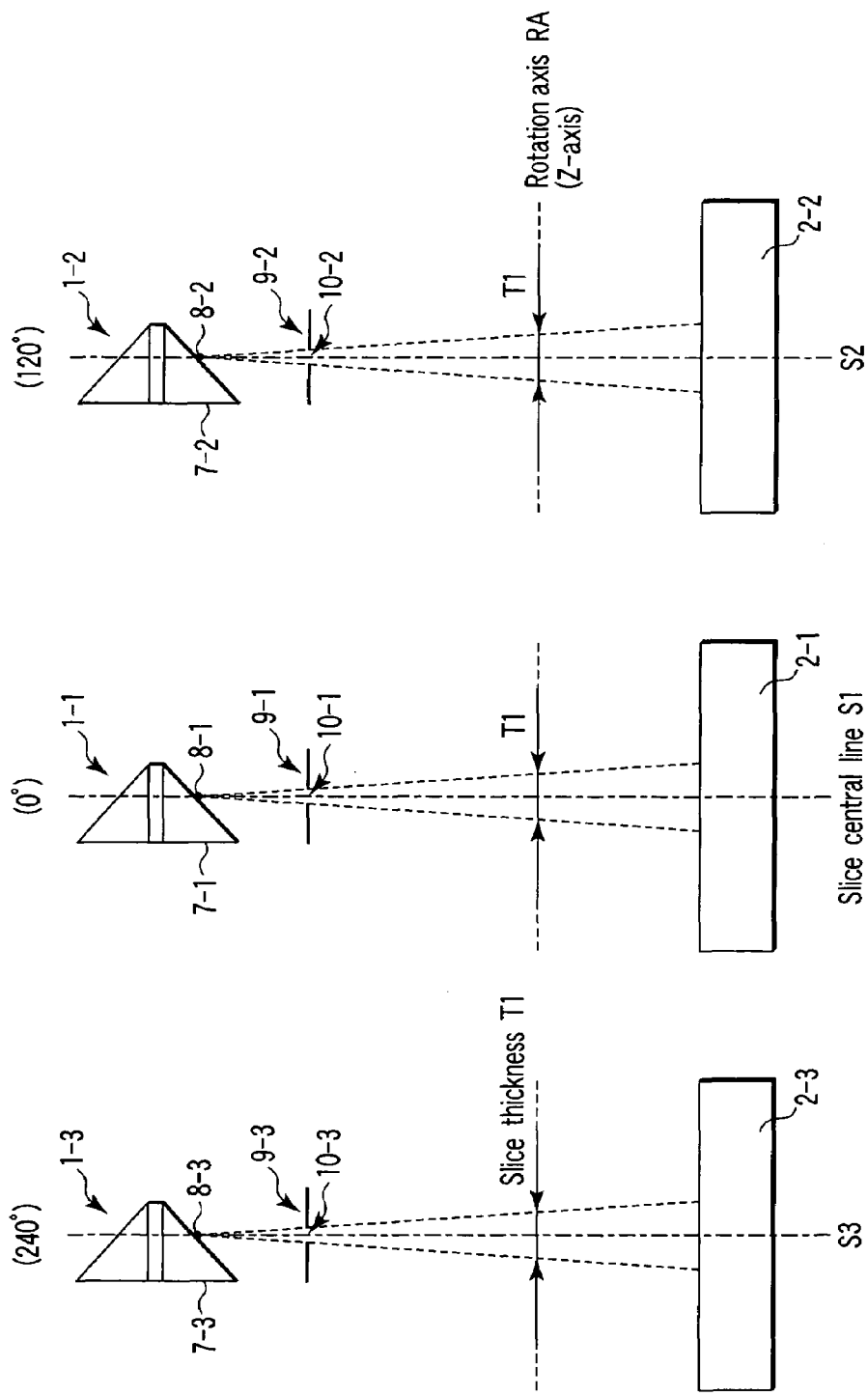

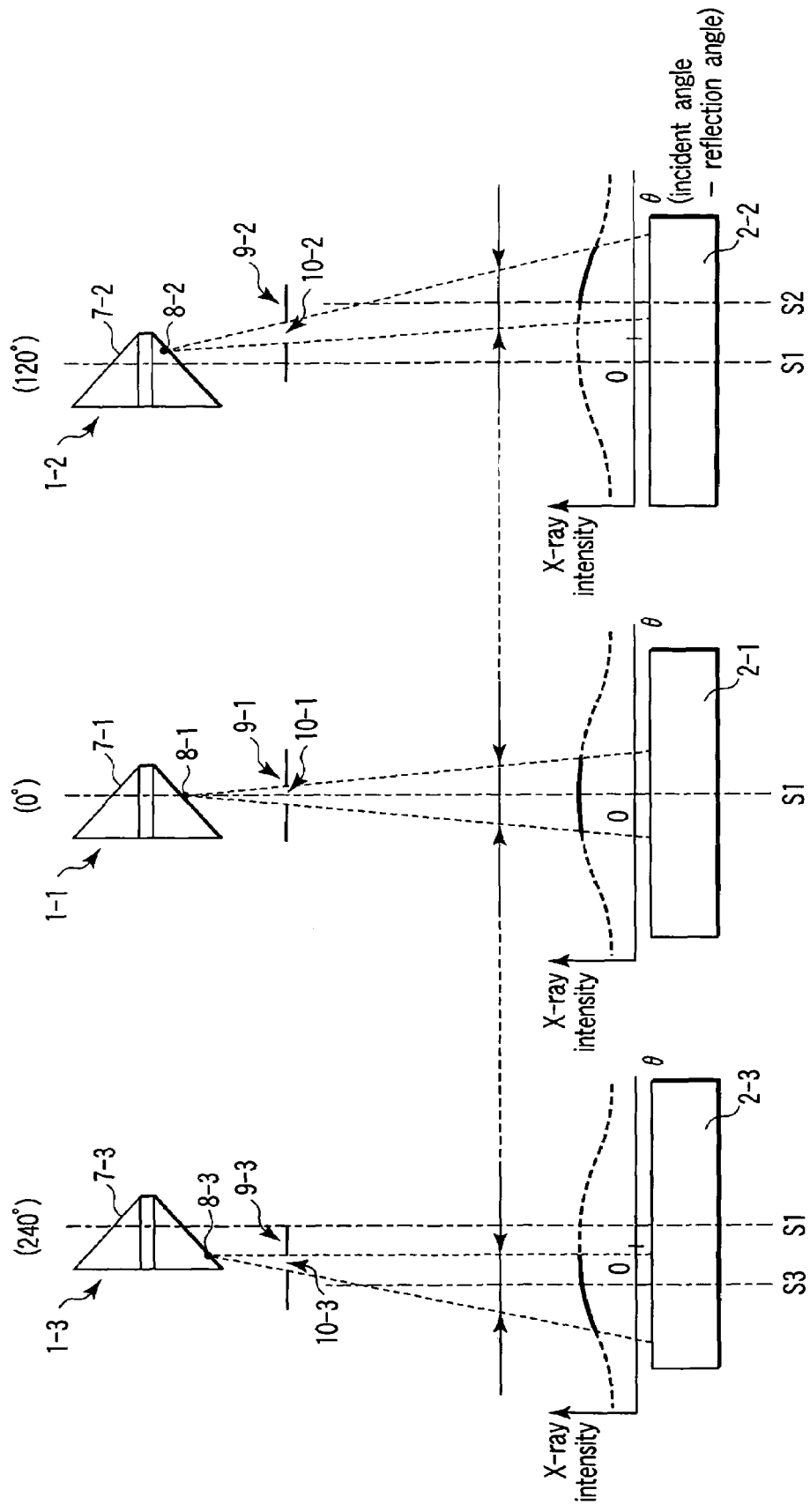

X-RAY COMPUTER TOMOGRAPHY APPARATUS

CROSS-REFERENCE TO RELATED APPLICATIONS

This application is based upon and claims the benefit of priority from prior Japanese Patent Application No. 2004-267217, filed Sep. 14, 2004, the entire contents of which are incorporated herein by reference.

BACKGROUND OF THE INVENTION

1. Field of the Invention

The present invention relates to an X-ray computer tomography apparatus.

2. Description of the Related Art

As is well known, an X-ray computer tomography apparatus is an apparatus which realizes the reconstruction of the attenuation coefficient distribution of a slice, i.e., a tomographic image, on the basis of projection data acquired by scanning a subject to be examined with X-rays in many directions.

X-ray computer tomography apparatuses of this type mainly use conventional scanning and helical scanning as schemes of scanning wide ranges. As is well known, conventional scanning is data acquiring operation of, for example, displacing the scan position a predetermined distance at a time by intermittently moving a bed top and repeating scanning in synchronism with the stopping of the movement. Helical scanning is operation of acquiring data by, for example, helical movement made by continuously moving a bed top and continuously rotating an X-ray tube.

Great importance is attached to high-speed data acquisition in wide areas by conventional scanning and helical scanning. For this purpose, studies have been made on the formation of an array of multiple X-ray detectors. Recently, a 32-detector array system has been developed toward practical use.

Main prior art references include Jpn. Pat. Appln. KOKAI Publication Nos. 5-38957 and 5-168616.

BRIEF SUMMARY OF THE INVENTION

It is an object of the present invention to provide an X-ray computer tomography apparatus which can scan a wide range at a high speed.

According to a first aspect of the present invention, there is provided an X-ray computer tomography apparatus comprising a substantially annular rotating frame supported to be rotatable around a rotation axis, a plurality of X-ray tubes discretely provided along a circumference of the rotating frame, a plurality of X-ray detectors discretely provided along the circumference of the rotating frame, a plurality of variable-opening slits which are made to respectively correspond to the plurality of X-ray tubes, and a slit control unit which individually controls widths and central positions of openings of the plurality of slits.

According to a second aspect of the present invention, there is provided an X-ray computer tomography apparatus comprising a substantially annular rotating frame supported to be rotatable around a rotation axis, a plurality of X-ray tubes discretely provided along a circumference of the rotating frame, a plurality of X-ray detectors which are provided in correspondence with the respective X-ray tubes such that central positions in a slice direction coincide with each other, a plurality of variable-opening slits which are provided in correspondence with the plurality of X-ray tubes, and a control unit which controls central positions of the openings of the slits, rotation of the rotating frame, generation of X-rays from the X-ray tubes, and X-ray detection by the X-ray detectors in a state in which the central positions of the openings of the plurality of slits in the rotation axis direction differ from each other.

According to a third aspect of the present invention, there is provided an X-ray computer tomography apparatus comprising a substantially annular rotating frame supported to be rotatable around a rotation axis, a plurality of X-ray tubes discretely provided along a circumference of the rotating frame, a plurality of X-ray detectors which are provided in correspondence with the respective X-ray tubes, a focal point control unit which individually controls X-ray focal positions of the plurality of X-ray tubes on rotating anodes in the rotation axis direction, and a control unit which controls the focal point control unit, rotation of the rotating frame, generation of X-rays from the X-ray tubes, and X-ray detection by the X-ray detectors so as to perform scanning in a state in which X-ray focal positions of the plurality of X-ray tubes differ from each other.

According to a fourth aspect of the present invention, there is provided an X-ray computer tomography apparatus comprising a substantially annular rotating frame supported to be rotatable around a rotation axis, a plurality of X-ray tubes discretely provided along a circumference of the rotating frame, a plurality of X-ray detectors which are provided in correspondence with the respective X-ray tubes, a plurality of tilt mechanisms which are provided in correspondence with the respective X-ray tubes to tilt each X-ray tube with respect to the rotation axis, and a control unit which controls the tilt mechanisms, rotation of the rotating frame, generation of X-rays from the X-ray tubes, and X-ray detection by the X-ray detectors so as to perform scanning in a state in which tilt angles of the plurality of X-ray tubes differ from each other.

According to a fifth aspect of the present invention, there is provided an X-ray computer tomography apparatus comprising a substantially annular rotating frame supported to be rotatable around a rotation axis, a plurality of X-ray tubes discretely provided along a circumference of the rotating frame, a plurality of X-ray detectors which are provided in correspondence with the respective X-ray tubes, a plurality of slide mechanisms which are provided in correspondence with the respective X-ray tubes so as to slide the each X-ray tube in a direction substantially parallel to the rotation axis, and a control unit which controls the slide mechanisms, rotation of the rotating frame, generation of X-rays from the X-ray tubes, and X-ray detection by the X-ray detectors so as to perform scanning in a state in which positions of the plurality of X-ray tubes in the rotation axis direction differ from each other.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing the main part of an X-ray computer tomography apparatus according to an embodiment of the present invention;

FIG. 3A is a view showing the first position of an X-ray tube 1-3 set by a position controller in FIG. 1;

FIG. 3B is a view showing the first position of an X-ray tube 1-1 set by the position controller in FIG. 1;

FIG. 3C is a view showing the first position of an X-ray tube 1-2 set by the position controller in FIG. 1;

FIG. 7A is a view showing the third position of the X-ray tube 1-3 set by the position controller in FIG. 1;

FIG. 7B is a view showing the third position of the X-ray tube 1-1 set by the position controller in FIG. 1;

FIG. 7C is a view showing the third position of the X-ray tube 1-2 set by the position controller in FIG. 1;

DETAILED DESCRIPTION OF THE INVENTION

An X-ray computer tomography apparatus (X-ray CT apparatus) according to a preferred embodiment of the present invention will be described below with reference to the views of the accompanying drawing. Note that the scanning schemes of X-ray computer tomography apparatuses include various types, e.g., a rotate/rotate type in which an X-ray tube and X-ray detector rotate together around a subject to be examined, and a stationary/rotate type in which many detection elements are arrayed in the form of a ring, and only an X-ray tube rotates around a subject to be examined. The present invention can be applied to either type. In this case, the rotate/rotate type will be exemplified. In order to reconstruct tomographic image data of one slice, one set of about 360° projection data corresponding to one rotation around a subject to be examined is required, or (180°+fan angle) projection data is required in the half scan method. The former method will be exemplified here. Note that projection data is defined as integral data associated with the passing distances of attenuation coefficients (or absorption coefficients) of tissue on an X-ray path.

FIG. 1 shows the arrangement of the main part of the X-ray computer tomography apparatus according to this embodiment. The X-ray computer tomography apparatus according to this embodiment is comprised of a scan gantry 10, bed 20, and computer unit 30. The scan gantry 10 is a structure for acquiring projection data associated with a subject to be examined. This projection data is loaded into the computer unit 30 and subjected to processing such as image reconstruction. The subject is inserted into substantially the cylindrical imaging area of the scan gantry 10 while lying on a top 21 of the bed 20.

Figure 2:
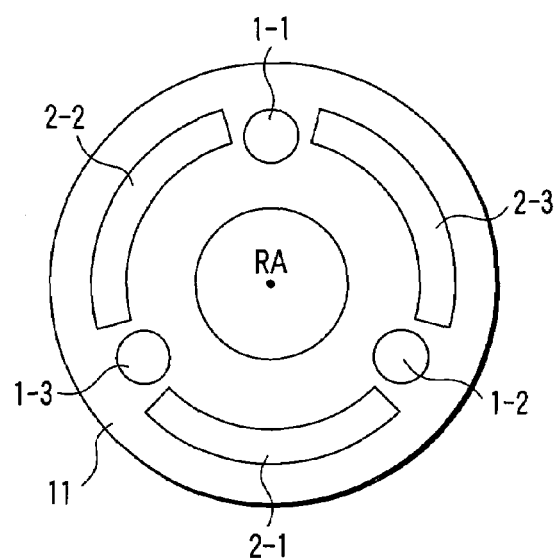
FIG. 2 is a view showing the arrangement of three X-ray tubes and three detectors in FIG. 1.

As also shown in FIG. 2, the scan gantry 10 is of a multi-tube type. An annular rotating frame 11 is supported by a rotating mechanism 4 so as to be rotatable around a rotation axis RA. A plurality of X-ray tubes, three X-ray tubes 1-1, 1-2, and 1-3 in this case, are fixed to the rotating frame 11 at 120° intervals around the rotation axis RA. Three X-ray detectors 2-1, 2-2, and 2-3 are also fixed to the rotating frame 11 at 120° intervals so as to face the three X-ray tubes 1-1, 1-2, and 1-3, respectively. In general, when imaging is performed, the subject is placed in the scan gantry 10 such that the body axis almost coincides with the rotation axis RA.

The X-ray tubes 1-1, 1-2, and 1-3 are rotating anode type X-ray tubes each configured such that a substantially umbrella-like anode is so provided as to be rotatable around an anode rotation axis parallel to the rotation axis RA, and electron beams from a cathode are made to collide with a target on the anode surface to generate X-rays. Deflecting electrodes are arranged along electron beam flying paths from the cathodes to the anodes, together with focusing electrodes. Each deflecting electrode comprises upper, lower, left, and right deflecting electrode portions. The balance of currents to be supplied to the opposing deflecting electrode portions is adjusted by focus control units 5-1, 5-2, and 5-3 under the control of a position controller 35, thereby controlling the positions where electron beams collide with the targets on the anode surfaces. In this case, in particular, an X-ray focal point can be moved along the rotation axis RA by intentionally deflecting the current balance at the upper and lower deflecting electrode portions which face each other in the rotation radius direction.

Tube tilt/slide mechanisms 7-1, 7-2, and 7-3 are provided in correspondence with the X-ray tubes 1-1, 1-2, and 1-3. The tube tilt/slide mechanisms 7-1, 7-2, and 7-3 each have a structure and motor for sliding a corresponding one of the X-ray tubes 1-1, 1-2, and 1-3 backward and forward by several cm along the rotation axis RA.

Figures 9A, 9B, 9C:
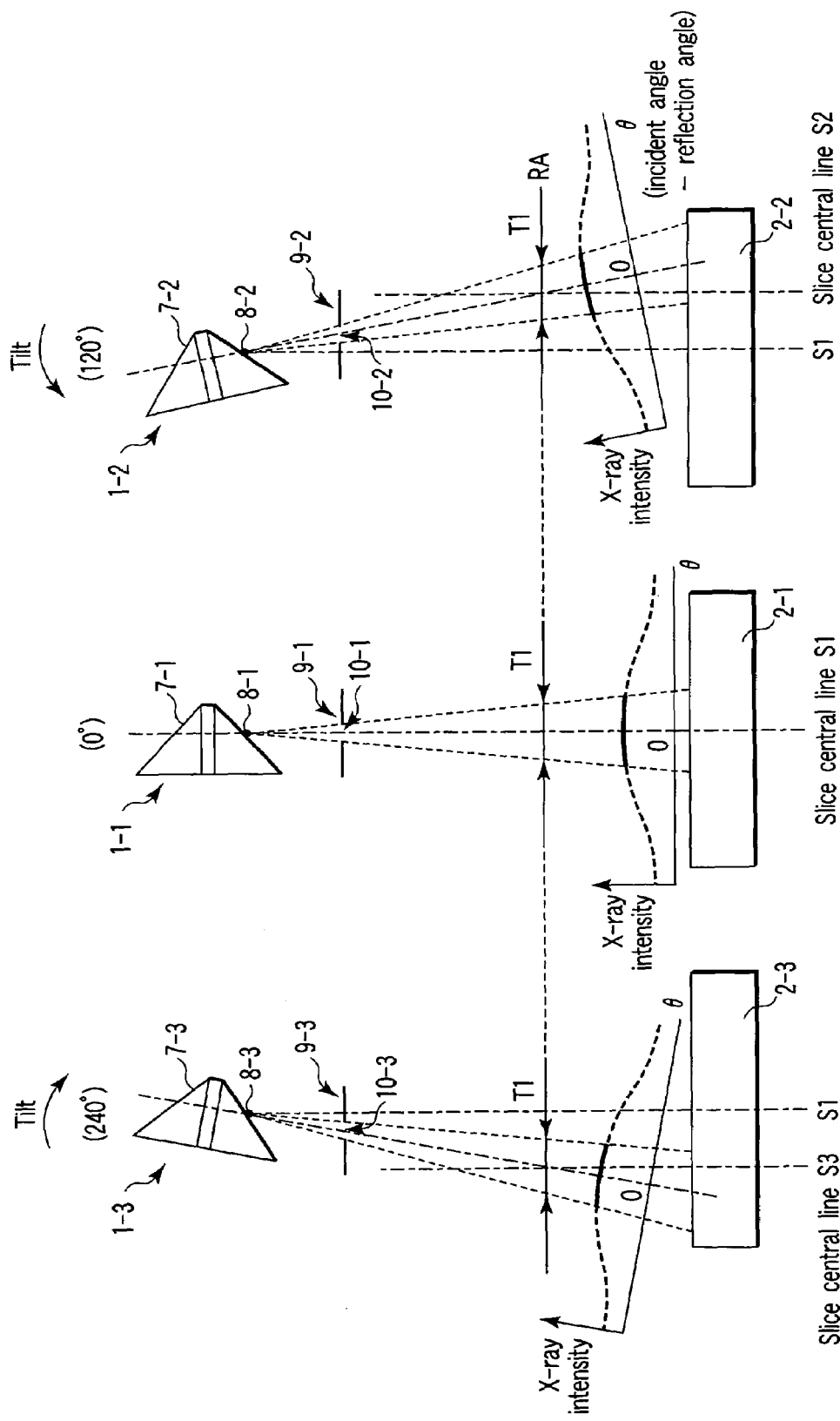
FIG. 9A is a view showing the tilt position of the X-ray tube 1-3 set by the position controller in FIG. 1.
FIG. 9B is a view showing the tilt position of the X-ray tube 1-1 set by the position controller in FIG. 1.
FIG. 9C is a view showing the tilt position of the X-ray tube 1-2 set by the position controller in FIG. 1.

The tube tilt/slide mechanisms 7-1, 7-2, and 7-3 each have a structure and motor for tilting a corresponding one of the X-ray tubes 1-1, 1-2, and 1-3 backward and forward through 5° with respect to the rotation axis RA (see FIGS. 9A, 9B, and 9C). More specifically, when the X-ray tubes 1-1, 1-2, and 1-3 are at reference positions, the rotation axes of their rotating anodes are almost parallel to the rotation axis RA. The tube tilt/slide mechanisms 7-1, 7-2, and 7-3 each tilt a corresponding one of the X-ray tubes 1-1, 1-2, and 1-3 such that the rotation axis of the rotating anode is tilted with respect to the rotation axis RA.

The X-ray detectors 2-1, 2-2, and 2-3 each have an array of a plurality of X-ray detection elements. The X-ray detectors 2-1, 2-2, and 2-3 each have a sensitive area (a sensitive width in the slice direction) having a width corresponding to the product of the maximum value of a plurality of slice thicknesses which can be selected by an operator and the number of tubes (three in this case) so as to cope with the movement of a slice in the slice direction (rotation axis RA direction (Z-axis)) (see FIGS. 3A, 3B, and 3C), as will be described later.

Slit mechanisms 9-1, 9-2, and 9-3 for limiting the slice thicknesses are arranged between the X-ray tubes 1-1, 1-2, and 1-3 and the imaging area, in practice in the X-ray emission windows of the X-ray tubes 1-1, 1-2, and 1-3. The slit mechanisms 9-1, 9-2, and 9-3 each have at least two light-shielding plates juxtaposed along the slice direction. The two light-shielding plates are supported to be separately movable along the slice direction. The positions of the two light-shielding plates are individually changed under the control of a corresponding one of slit control units 6-1, 6-2, and 6-3, thereby arbitrarily adjusting the opening width in the slice direction and shifting the central position of the opening along the slice direction (see FIGS. 3A, 3B, 3C, 5A, 5B, and 5C).

The data acquisition devices 3-1, 3-2, and 3-3 are respectively connected to the X-ray detectors 2-1, 2-2, and 2-3. Outputs from the X-ray detectors 2-1, 2-2, and 2-3 are supplied and stored as projection data in a data storage unit 33 through the data acquisition devices 3-1, 3-2, and 3-3, a slip ring (not shown) which allows continuous rotation, and a pre-processing unit 32.

In addition to the pre-processing unit 32 and data storage unit 33, the computer unit 30 comprises a system controller 31 which controls the overall apparatus, a scan controller 36 which controls the rotating mechanism 4, the data acquisition devices 3-1, 3-2, and 3-3, and a high voltage generator (not shown) to execute scanning operation, a reconstruction unit 34 which reconstructs tomographic image data on the basis of a stored projection data set, an input device 37 such a keyboard, mouse, or the like, a display 38 which displays a tomographic image and the like, the position controller 35, a zero correction data storage unit 41, and a zero correction processing unit 43.

Figures 5A, 5B, 5C:
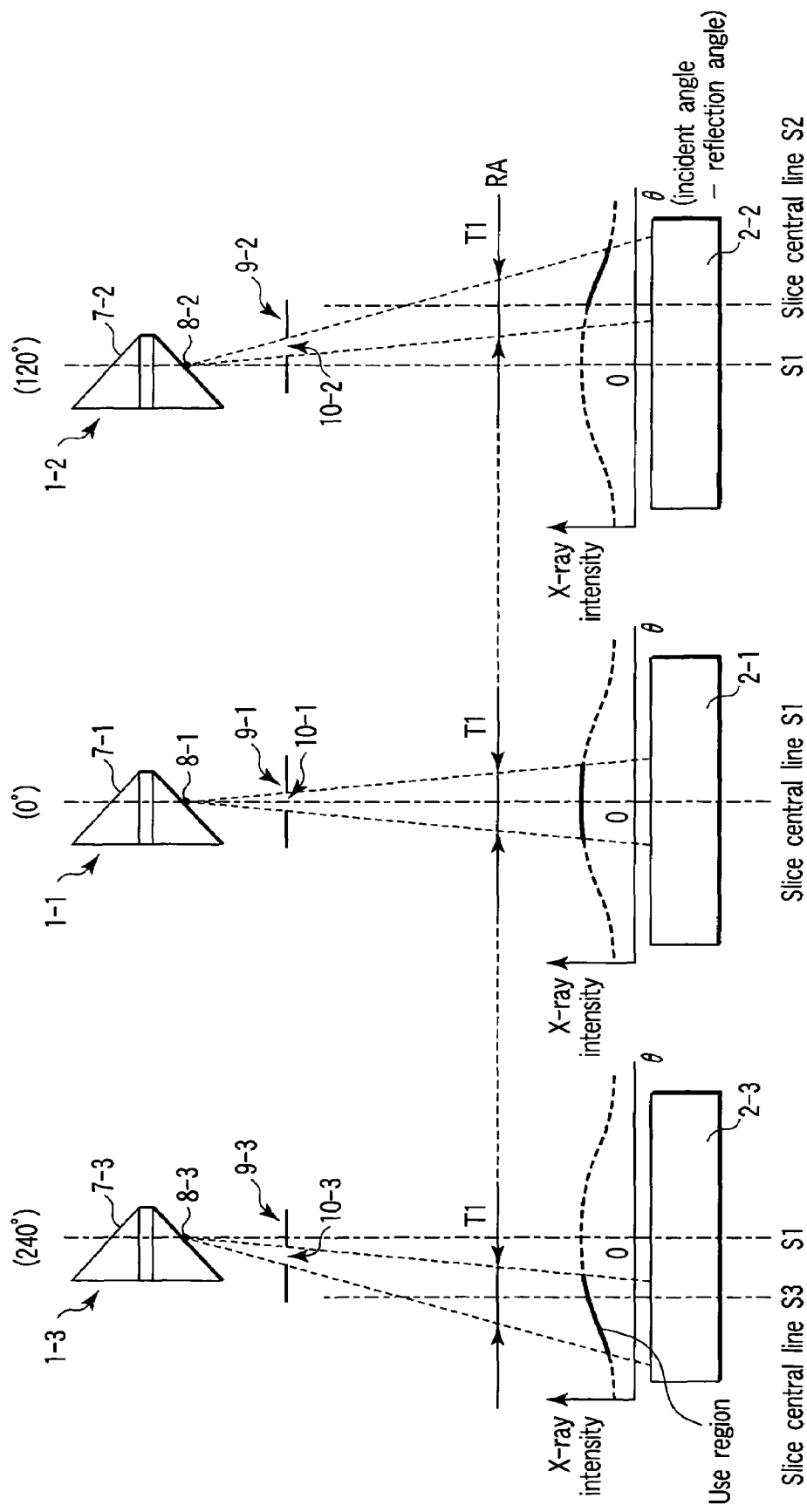
FIG. 5A is a view showing the second position of the X-ray tube 1-3 set by the position controller in FIG. 1.
FIG. 5B is a view showing the second position of the X-ray tube 1-1 set by the position controller in FIG. 1.
FIG. 5C is a view showing the second position of the X-ray tube 1-2 set by the position controller in FIG. 1.

The zero correction processing unit 43 is provided to correct outputs from the X-ray detectors 2-1, 2-2, and 2-3 for each detection element so as to correct spatial variations in the X-ray intensity and X-ray detection sensitivity with respect to projection data having undergone pre-processing. As is well known, X-ray intensity is not constant and exhibits a maximum value in a direction in which the incident angle and reflection angle of an electron beam with respect to an anode surface coincide with each other, and decreases with an increase in the difference between the incident angle and the reflection angle, as shown in FIGS. 5A, 5B, and 5C. As will be described later with reference to FIGS. 5A, 5B, and 5C, different regions of an X-ray intensity distribution are used among three slices. As a consequence, the reference intensity (zero point) varies for each slice. When image data is reconstructed by using the projection data of these three slices as unity data, an artifact is caused by differences in zero point. In order to reduce this artifact, zero point correction is performed by the zero correction processing unit 43. A plurality of data sets (a plurality of zero correction data sets) used for the correction processing are stored in the zero correction data storage unit 41 in advance. The plurality of zero correction data sets differ in the central angle $\theta$ of a region to be used. For example, a zero correction data set is generated for each 0.05°. A zero correction data set is generated for each of the detection elements of the X-ray detectors 2-1, 2-2, and 2-3. In addition, a zero correction data set is generated for each of the X-ray tubes 1-1, 1-2, and 1-3. A zero correction data set is typically a projection data set acquired by using a homogeneous phantom or data generated on the basis thereof. The identification codes of the X-ray tubes 1-1, 1-2, and 1-3 and codes for identifying angles $\theta$ are associated with a plurality of zero correction data sets. This allows the zero correction processing unit 43 to selectively read out corresponding zero correction data sets from the zero correction data storage unit 41 in accordance with information such as the angles $\theta$ and the central positions of the openings of the slits from the position controller 35.

The position controller 35 controls the opening widths of the slit mechanisms 9-1, 9-2, and 9-3 in accordance with the slice thicknesses input through the input device 37, and controls the positions of the X-ray focal points of the X-ray tubes 1-1, 1-2, and 1-3 in the slice direction and the central positions of the openings of the slit mechanisms 9-1, 9-2, and 9-3 in accordance with the selection of a scan mode (the normal scan mode or high-speed scan mode). In addition, the position controller 35 controls the tilt/slide mechanical units in accordance with information associated with tilt/slide/focal point movement input through the input device 37. Note that one or a combination of two of tilting operation, sliding operation, and focal point moving operation is used. Performing tilt/slide/focal point movement makes it possible to bring the angle $\theta$ of an X-ray use region to or near 0°.

Figure 4:
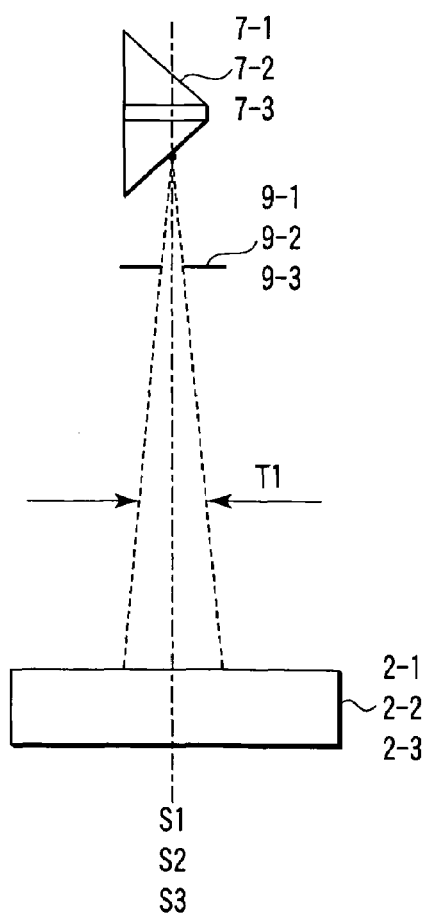
FIG. 4 is a view comprehensively showing the first position set by the position controller in FIG. 1.

FIGS. 3A, 3B, and 3C each show the X-ray focal position and opening width in the normal scan mode. In the normal scan mode, the slit control units 6-1, 6-2, and 6-3 each adjust a corresponding one of openings 10-1, 10-2, and 10-3 of the slit mechanisms 9-1, 9-2, and 9-3 to an opening width corresponding to a slice thickness T1 set by the operator, and uniformly set each of the central positions of the openings to a reference position under the control of the position controller 35. In addition, in the normal scan mode, the focus control units 5-1, 5-2, and 5-3 uniformly set the focal positions of the X-ray tubes 1-1, 1-2, and 1-3 to reference positions under the control of the position controller 35. X-rays from the X-ray tubes 1-1, 1-2, and 1-3 are superimposed on each other as shown in FIG. 4. In this normal scan mode, for conventional scanning, the top 21 is repeatedly moved by a distance T1 and stopped. For helical scanning, the top 21 is adjusted to be moved by the distance T1 per rotation of the X-ray tube. In the normal scan mode, when single-slice scanning is to be performed, the time resolution of a tomographic image can be substantially reduced to ⅓ (speeding up) by reconstructing the tomographic image by using outputs from a plurality of (three in this case) X-ray detectors.

In the high-speed scan mode (wide-area scan mode), as shown in FIGS. 5A, 5B, and 5C, the slit control units 6-1, 6-2, and 6-3 adjust the openings 10-1, 10-2, and 10-3 of the slit mechanisms 9-1, 9-2, and 9-3 to the opening width corresponding to the slice thickness T1 set by the operator under the control of the position controller 35. The central position of the opening of the slit mechanism 9-1 is maintained at a reference position (FIG. 5B). The central position of the opening of the slit mechanism 9-2 is moved from the reference position in the plus direction of the slice axis by a distance corresponding to the slice thickness T1 (FIG. 5C). The central position of the opening of the slit mechanism 9-3 is moved from the reference position in the minus direction of the slice axis by a distance corresponding to the slice thickness T1 (FIG. 5A).

Figure 6:
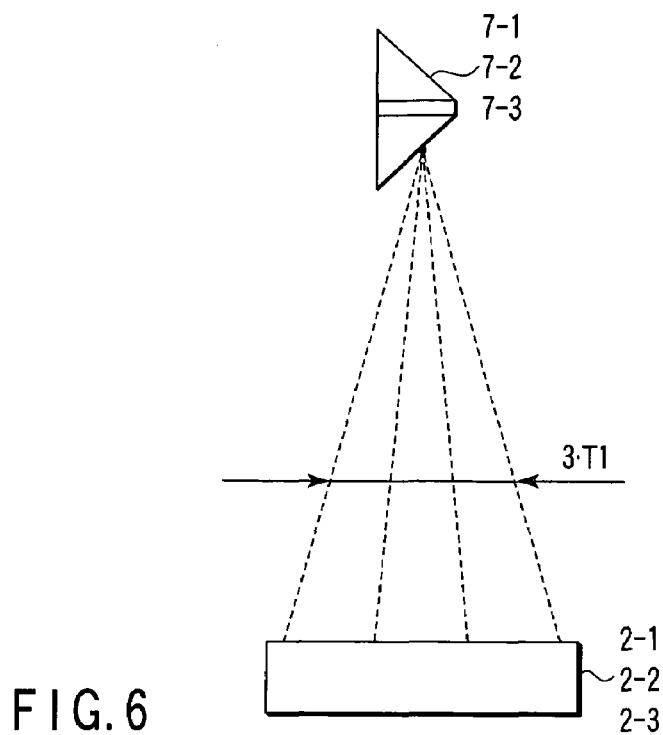
FIG. 6 is a view comprehensively showing the second position set by the position controller in FIG. 1.
Figure 8:
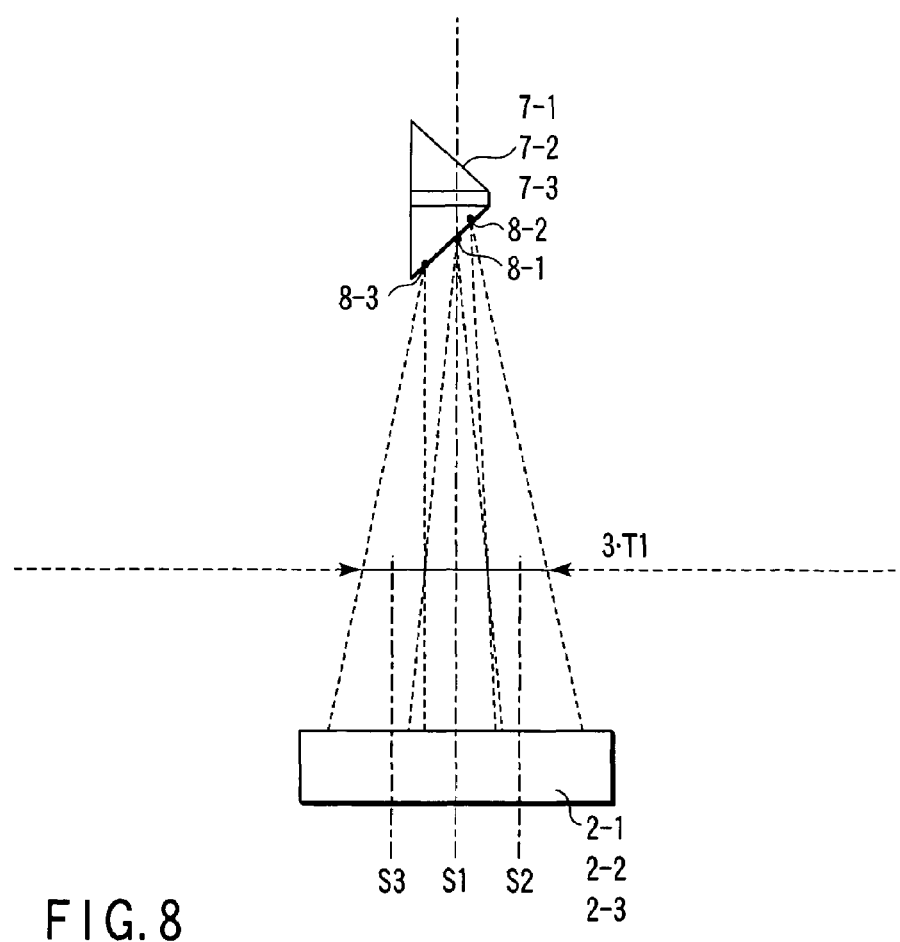
FIG. 8 is a view comprehensively showing the third position set by the position controller in FIG. 1.

As shown in FIG. 6, with this opening central position control, the above arrangement functions to be substantially equivalent to a three-array system in which three slices are continuous. That is, data corresponding to three arrays can be acquired at once by one rotation. In this high-speed scan mode, for conventional scanning, the top 21 is repeatedly moved by "slice thickness T1×tube count" and stopped. For helical scanning, the moving speed of the top 21 is adjusted such that the top 21 is moved by a distance of "slice thickness T1×tube count" per X-ray tube rotation. As compared with the normal scan mode, in the high-speed scan mode, scanning in the same range can be completed in a time corresponding to 1/tube count multiple of the time taken in the normal scan mode. In other words, as compared with the normal scan mode, in the high-speed scan mode, a range corresponding to a tube count multiple can be scanned in the same time.

In the high-speed scan mode, as shown in FIGS. 7A, 7B, 7C, and 8, X-ray focal points 8-1, 8-2, and 8-3 of the X-ray tubes 1-1, 1-2, and 1-3 may be shifted, together with the movement of the central positions of the openings 10-1, 10-2, and 10-3 of the slit mechanisms 9-1, 9-2, and 9-3. The focus control units 5-1, 5-2, and 5-3 maintain the X-ray focal position of the X-ray tube 1-1 at the reference position (FIG. 7B), move the X-ray focal position of the X-ray tube 1-2 from the reference position in the plus direction of the slice axis by a distance corresponding to the slice thickness T1 (FIG. 7C), and move the X-ray focal position of the X-ray tube 1-3 from the reference position in the minus direction of the slice axis by a distance corresponding to the slice thickness T1 (FIG. 7A) under the control of the position controller 35. By moving the central positions of the openings, together with shifting the X-ray focal points, the X-ray central lines of the X-ray tubes 1-2 and 1-3 on the two sides can be made perpendicular or nearly perpendicular to the rotation axis RA. This makes it possible to reduce the occurrence of an artifact due to an increase in so-called cone angle. In addition, as described above, by moving the focal points, the angles θ of the X-ray use regions of the X-ray tubes 1-2 and 1-3 on the two sides can be set to 0° or nearly 0°, thereby improving image quality/zero point correction precision.

In addition, in place of focal point movement, in the high-speed scan mode, sliding of the X-ray tubes 1-1, 1-2, and 1-3 can be performed, together with movement of the central positions of the openings 10-1, 10-2, and 10-3 of the slit mechanisms 9-1, 9-2, and 9-3. As in the case of focal point movement, with the operation of the tube tilt/slide mechanisms 7-1, 7-2, and 7-3, the X-ray focal position of the X-ray tube 1-1 is maintained at the reference position, the X-ray focal position of the X-ray tube 1-2 is moved from the reference position in the plus direction of the slice axis by a distance corresponding to the slice thickness T1, and the X-ray focal position of the X-ray tube 1-3 is moved from the reference position in the minus direction of the slice axis by a distance corresponding to the slice thickness T1 under the control of the position controller 35. As described above, by moving the opening central positions and sliding the X-ray tubes concurrently, the X-ray central lines of the X-ray tubes 1-2 and 1-3 on the two sides can be made perpendicular or nearly perpendicular to the rotation axis RA. This makes it possible to reduce the occurrence of an artifact due to an increase in so-called cone angle. In addition, the angles θ of the X-ray use regions of the X-ray tubes 1-2 and 1-3 on the two sides can be set to 0° or nearly 0°, thereby improving image quality/zero point correction precision.

Furthermore, as shown in FIGS. 9A, 9B, and 9C, by individually tilting the X-ray tubes 1-1, 1-2, and 1-3, together with sliding the tubes, the angles θ of the X-ray use regions of the X-ray tubes 1-2 and 1-3 on the two sides can be set to 0° or nearly 0°, thereby improving image quality/zero point correction precision.

In the high-speed scan mode, while the central positions of the openings 10-1, 10-2, and 10-3 are fixed to the reference positions, the slice positions may be moved by shifting the x-ray focal points 8-1, 8-2, and 8-3 of the X-ray tubes 1-1, 1-2, and 1-3.

According to this embodiment, even a one-array system can scan a wide range at a high speed like a multi-array system. In addition, wide-area, high-speed scanning and single-slice, high-speed scanning (normal scan mode) can be switched. This switching operation can be realized without requiring any large-scale moving mechanism for the X-ray tubes or X-ray detectors.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus comprising:
a rotating frame supported to be rotatable around a rotation axis;
a plurality of X-ray tubes discretely provided on the rotating frame;
a plurality of X-ray detectors discretely provided on the rotating frame;
a plurality of variable-opening slits which are made to respectively correspond to said plurality of X-ray tubes; and
a slit control unit which individually controls widths and central positions of openings of said plurality of slits, wherein the slit control unit controls the openings of said plurality of slits such that a plurality of slices corresponding to said plurality of X-ray tubes become substantially continuous along the rotation axis.

2. An apparatus according to claim 1, wherein the slit control unit controls the openings of said plurality of slits such that central lines of slices respectively corresponding to said plurality of X-ray tubes substantially coincide with each other.

3. An apparatus according to claim 1, wherein the slit control unit controls the openings of said plurality of slits such that a state in which slices respectively corresponding to said plurality of X-ray tubes are continuous along the rotation axis and a state in which the central lines of the slices respectively corresponding to said plurality of X-ray tubes substantially coincide with each other are switched in accordance with an instruction from an operator.

4. An apparatus according to claim 1, wherein the slit control unit controls the openings of said plurality of slits such that thicknesses of slices respectively corresponding to said plurality of X-ray tubes substantially coincide with each other.

5. An apparatus according to claim 1, further comprising a focal point control unit which individually controls X-ray focal positions of said plurality of X-ray tubes on rotating anodes by electron beam deflection control.

6. An apparatus according to claim 1, further comprising a correcting unit which corrects outputs from said plurality of X-ray detectors for each detection element so as to correct spatial variations in X-ray intensity and X-ray detection sensitivity.

7. An apparatus according to claim 6, further comprising a reconstruction unit which reconstructs image data by using the corrected outputs from said plurality of X-ray detectors as unity data.

8. An X-ray computer tomography apparatus comprising:
a rotating frame supported to be rotatable around a rotation axis;

a plurality of X-ray tubes discretely provided on the rotating frame;

a plurality of X-ray detectors which are provided in correspondence with the respective X-ray tubes such that central positions in a slice direction coincide with each other;

a plurality of variable-opening slits which are provided in correspondence with said plurality of X-ray tubes; and a control unit which controls central positions of the openings of the slits, rotation of the rotating frame, generation of X-rays from the X-ray tubes, and X-ray detection by the X-ray detectors in a state in which the central positions of the openings of said plurality of slits in the rotation axis direction differ from each other.

9. An apparatus according to claim 8, further comprising a focal point control unit which individually controls X-ray focal positions of said plurality of X-ray tubes on rotating anodes by electron beam deflection control.

10. An apparatus according to claim 8, further comprising a correcting unit which corrects outputs from said plurality of X-ray detectors for each detection element so as to correct spatial variations in X-ray intensity and X-ray detection sensitivity.

11. An apparatus according to claim 10, further comprising a reconstruction unit which reconstructs image data by using the corrected outputs from said plurality of X-ray detectors as unity data.

12. An X-ray computer tomography apparatus comprising:

a rotating frame supported to be rotatable around a rotation axis;

a plurality of X-ray tubes discretely provided on the rotating frame;

a plurality of X-ray detectors which are provided in correspondence with the respective X-ray tubes;

a focal point control unit which individually controls X-ray focal positions of said plurality of X-ray tubes on rotating anodes in the rotation axis direction; and a control unit which controls the focal point control unit, rotation of the rotating frame, generation of X-rays from the X-ray tubes, and X-ray detection by the X-ray detectors so as to perform scanning in a state in which X-ray focal positions of said plurality of X-ray tubes differ from each other.

13. An apparatus according to claim 12, further comprising a plurality of variable-opening slits which are provided in correspondence with said plurality of X-ray tubes to make a plurality of slices corresponding to said plurality of X-ray tubes substantially continuous along the rotation axis.

14. An X-ray computer tomography apparatus comprising:

a rotating frame supported to be rotatable around a rotation axis;

a plurality of X-ray tubes discretely provided on the rotating frame;

a plurality of X-ray detectors which are provided in correspondence with the respective X-ray tubes;

a plurality of tilt mechanisms which are provided in correspondence with the respective X-ray tubes to tilt each X-ray tube with respect to the rotation axis; and a control unit which controls the tilt mechanisms, rotation of the rotating frame, generation of X-rays from the X-ray tubes, and X-ray detection by the X-ray detectors so as to perform scanning in a state in which tilt angles of said plurality of X-ray tubes differ from each other.

15. An apparatus according to claim 14, further comprising a plurality of variable-opening slits which are provided in correspondence with said plurality of X-ray tubes to make a plurality of slices corresponding to said plurality of X-ray tubes substantially continuous along the rotation axis.

16. An X-ray computer tomography apparatus comprising:

a rotating frame supported to be rotatable around a rotation axis;

a plurality of X-ray tubes discretely provided on the rotating frame;

a plurality of X-ray detectors which are provided in correspondence with the respective X-ray tubes;

a plurality of slide mechanisms which are provided in correspondence with the respective X-ray tubes so as to slide each X-ray tube in a direction substantially parallel to the rotation axis; and a control unit which controls the slide mechanisms, rotation of the rotating frame, generation of X-rays from the X-ray tubes, and X-ray detection by the X-ray detectors so as to perform scanning in a state in which positions of said plurality of X-ray tubes in the rotation axis direction differ from each other.

17. An apparatus according to claim 16, further comprising a plurality of variable-opening slits which are provided in correspondence with said plurality of X-ray tubes to make a plurality of slices corresponding to said plurality of X-ray tubes substantially continuous along the rotation axis.

18. An X-ray computer tomography apparatus comprising:

a rotating frame supported to be rotatable around a rotation axis;

a first X-ray tube and second X-ray tube which are discretely provided on the rotating frame; and a first X-ray detector and second X-ray detector which are provided in correspondence with the first X-ray tube and second X-ray tube, wherein a center of an X-ray emission range in a slice direction of the first X-ray tube is shifted from a center of the first detector toward one side, and a center of an X-ray emission range of the second X-ray tube is shifted from a center of the second detector toward a side opposite to the center of the emission range of the first X-ray tube.

19. An X-ray computer tomography apparatus comprising:

a rotating frame supported to be rotatable around a rotation axis;

a first X-ray tube and second X-ray tube which are discretely provided on the rotating frame; and a first X-ray detector and second X-ray detector which are provided in correspondence with the first X-ray tube and second X-ray tube, wherein a center of an X-ray emission range in a slice direction of the first X-ray tube is shifted from a center of the first detector toward one side, and a center of an X-ray emission range of the second X-ray tube substantially coincides with a center of the second detector.

* * * * *